United States Patent [19]
Green et al.

[11] Patent Number: 4,777,944
[45] Date of Patent: Oct. 18, 1988

[54] PATIENT RESTRAINING DEVICE WITH ALARM ACTIVATING MEANS

[76] Inventors: Frank H. Green, 516 N. Morgan St., Rushville, Ind. 46173; David L. Green, 20 Oakshore Dr., Bratenahl, Ohio 44108

[21] Appl. No.: 903,416

[22] Filed: Sep. 2, 1986

Related U.S. Application Data

[63] Continuation-in-part of Ser. No. 573,692, Jan. 25, 1984, Pat. No. 4,608,973.

[51] Int. Cl.$^4$ .......................... A61F 13/00; A61B 5/10
[52] U.S. Cl. .................................... 128/874; 128/782; 340/573; 340/876
[58] Field of Search .............. 128/774, 133, 134, 721, 128/781, 782; 340/573, 668, 686, 575; 200/47, 153 L, 153 LA, 153 T, 161, 61.93, 38 E

[56] References Cited

U.S. PATENT DOCUMENTS

| | | |
|---|---|---|
| D. 256,850 | 9/1980 | Donahue . |
| 1,699,663 | 1/1929 | Hess . |
| 1,890,679 | 12/1932 | Hallenbeck . |
| 2,036,171 | 3/1936 | Fox . |
| 2,478,239 | 8/1949 | Chinn . |
| 2,621,265 | 12/1952 | Alcoriza ............................... 200/161 |
| 2,751,594 | 6/1956 | Brissenden . |
| 3,094,602 | 6/1963 | Frachon .......................... 200/153 T |
| 3,137,294 | 6/1964 | Robertson ............................ 128/134 |
| 3,182,338 | 5/1965 | Shirrod . |
| 3,236,234 | 2/1966 | Buckley . |
| 3,265,065 | 8/1966 | Jillson . |
| 3,638,647 | 2/1972 | Creelman . |
| 3,641,997 | 2/1972 | Posey, Jr. . |
| 3,670,320 | 6/1972 | Palmer . |
| 3,699,856 | 10/1972 | Chabot et al. ................... 128/482 X |
| 3,796,208 | 3/1974 | Bloice .............................. 340/573 X |
| 3,924,215 | 12/1975 | Allison . |
| 3,950,746 | 4/1976 | Davies .............................. 340/668 X |
| 3,980,988 | 9/1976 | Spizzo .............................. 340/575 X |
| 4,007,733 | 2/1977 | Celeste et al. . |
| 4,247,744 | 1/1981 | Birkle ........................... 200/153 T X |
| 4,263,586 | 4/1981 | Nicholas . |
| 4,295,133 | 10/1981 | Vance .............................. 340/575 X |
| 4,298,863 | 11/1981 | Natitus et al. ...................... 340/573 |
| 4,360,014 | 11/1982 | Manahan . |
| 4,417,572 | 11/1983 | Green . |
| 4,488,544 | 12/1984 | Triunfol ............................... 128/134 |
| 4,608,973 | 9/1986 | Green et al. . |

FOREIGN PATENT DOCUMENTS 569490 1/1959 Canada .
2959 of 1887 United Kingdom .

Primary Examiner—Robert A. Hafer
Assistant Examiner—Kathleen J. D'Arrigo
Attorney, Agent, or Firm—Woodard, Emhardt, Naughton, Moriarty & McNett

[57] ABSTRACT

A patient restraining device having an adjustable length bar configured to attach to the side rails of a bed and be located beneath the bed. Pivoted levers attached to the bar are connectable to straps passing around each side of the bed and connected to a restraining vest worn by the patient. The pivotable levers are in turn connected to a switch box attached to the bar so that tension in either one or both of the restraining straps causes the switch mechanism of the switch box to be activated, which in turn activates an internal or external alarm. The pivotable levers are arranged with compressible bushings so that tension in the straps must exceed a predetermined level for the levers to pivot far enough to activate the alarm.

8 Claims, 3 Drawing Sheets

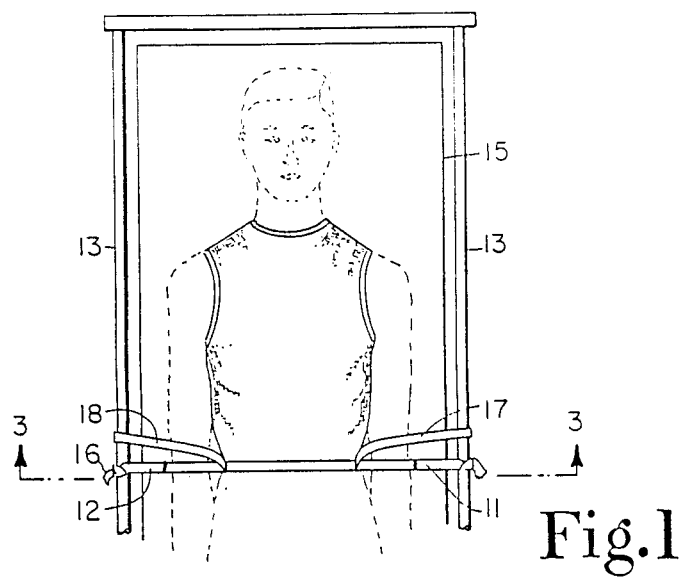
Fig.1
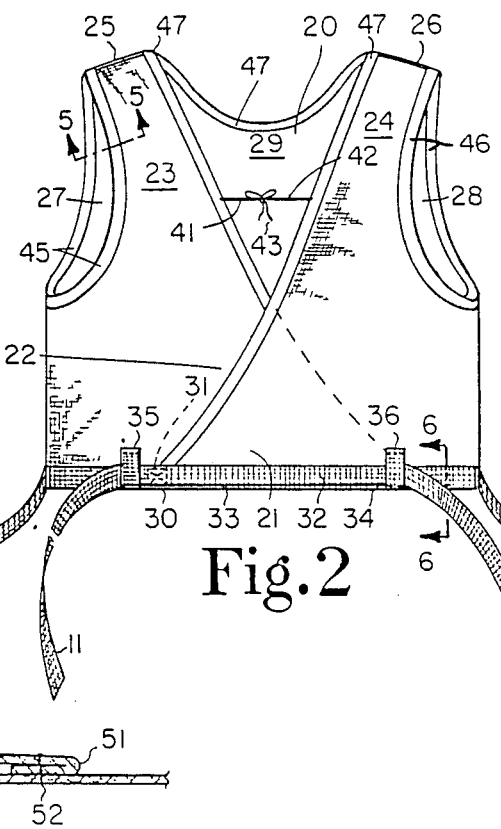
Fig.2
Fig.5
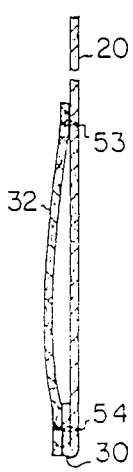
Fig.6

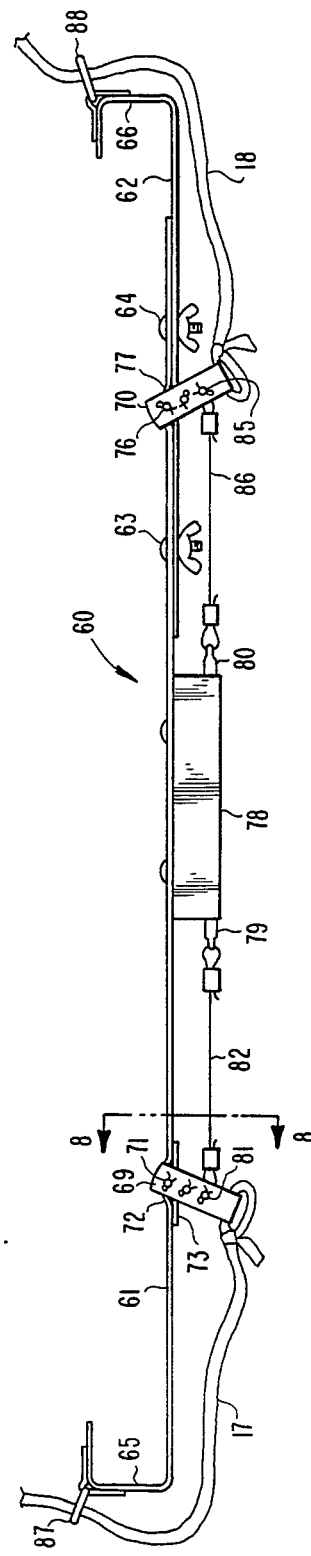
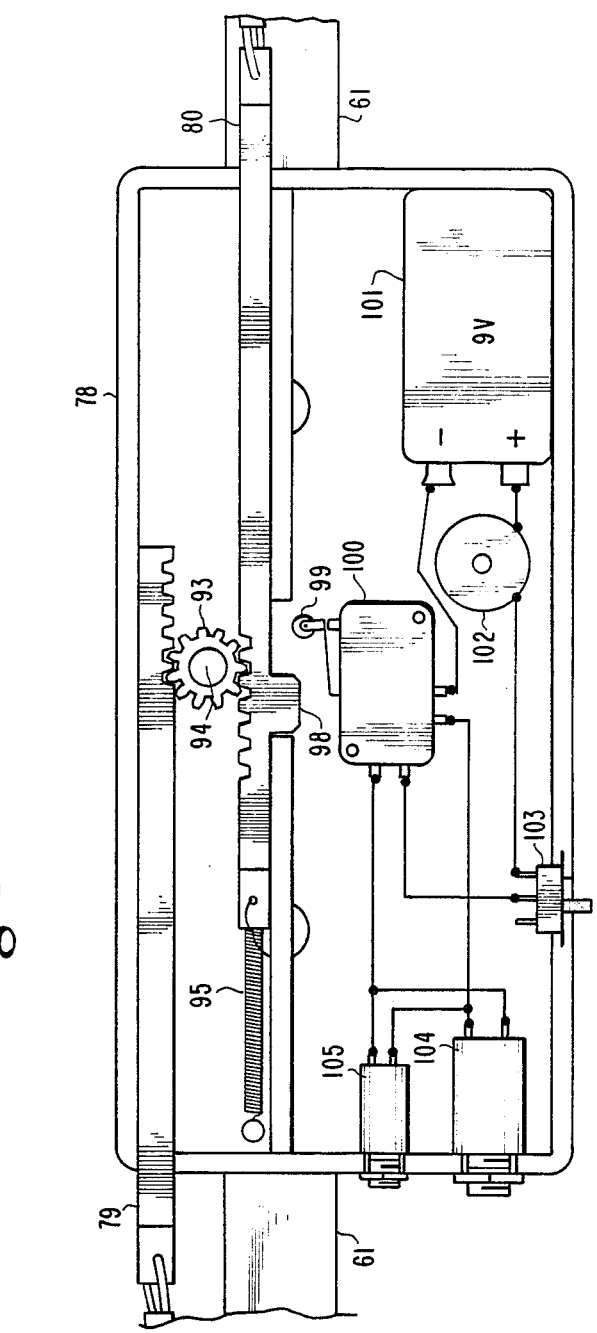
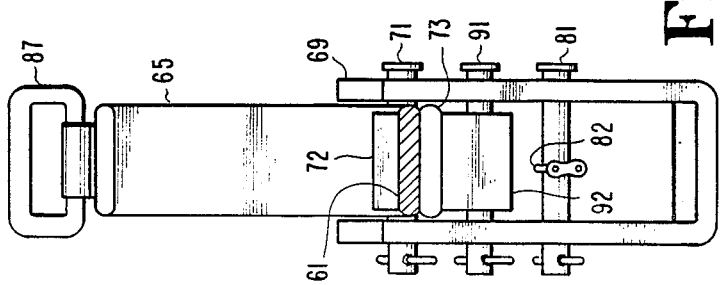
Fig.7
Fig.9
Fig.8

PATENT RESTRAINING DEVICE WITH ALARM ACTIVATING MEANS

REFERENCE TO RELATED APPLICATIONS

This application is a continuation-in-part of U.S. patent application Ser. No. 573,692, filed on Jan. 25, 1984 by the same inventive entity, and issued Sept. 2, 1986 under U.S. Pat. No. 4,608,973, entitled PATIENT RESTRAINING DEVICE.

BACKGROUND OF THE INVENTION

1. Field of the Invention

This invention relates to a device for restraining a patient in bed which is particularly adapted to activate an alarm signal indicative of excessive movement of the patient.

2. Description of the Prior Art

Various devices have been employed to restrain a patient in bed while allowing limited movement. One such device which is adapted for use with a conventional strap restraint and which further provides an alarm to indicate excessive movement of the patient is described in U.S. Pat. No. 4,417,572, issued to Green on Nov. 29, 1983. The Green device is normally effective in alerting monitoring personnel of a patient's excessive movement, but its effectiveness can be negated if the restraining belt to which it is attached slips off of or is removed by the patient. A further limitation of the Green device is that it is limited to use with a particular form of conventional nurse call button, and is somewhat cumbersome to attach to the patient's bed.

Thus, it would be desirable to provide a restraining garment which is inexpensive, is adjustable to fit persons of various sizes, does not cause excessive localized irritation, and is not easily removed by the patient. An improved monitoring device which can be used with such a garment would activate any nurse call system or a stand-alone or self-contained alarm system.

SUMMARY OF THE INVENTION

A patient restraint device for use by a patient to be restrained on a bed against excessive vertical and horizontal movement with respect to the bed, and for alerting nursing personnel of impending excessive movement before the patient is endangered thereby, includes a vest securely received about the upper body of the patient, an alarm, and bidirectional alarm activating switch means located beneath and fixed to the bed out of reach of the patient, and responsive to pulling force applied thereto in either of two opposite horizontal directions, for activating the alarm in response to pulling force exceeding a predetermined limit applied in any of the opposite horizontal directions. Further included are means for translating vertical or horizontal motion of the patient into pulling force applied in at least one of the opposite first and second horizontal directions, the translation means including a first monitor strap having first and second ends, the first end securely attached to the vest, the first strap extending from the vest over one side of the bed, the second end thereof connected to the bidirectional alarm activating switch means such that tension in the first monitor strap exerts a pulling force in the first direction, and a second monitor strap having first and second ends, the first end securely attached to the vest, the second strap extending from the vest over the other side of the bed, the second end thereof connected to the bidirectional alarm activating switch means such that tension in the second monitor strap exerts a pulling force in the second direction.

It is an object of the present invention to provide an improved monitoring device for use with a restraining vest for restraining a patient in bed.

Other objects and advantages of the present invention will be apparent from the following descriptions.

BRIEF DESCRIPTION OF THE DRAWINGS

FIG. 1 is a plan view of the restraining vest portion of the present invention in use.

FIG. 2 is an elevational view of of the restraining vest of FIG. 1, showing the vest from the back.

FIG. 5 is a detail sectional view of one of the seams of the restraining vest taken substantially upon a plane passing through section line 5—5.

FIG. 6 is a detail sectional view of one of the seams of the restraining vest taken substantially upon a plane passing through section line 6—6.

FIG. 7 is an elevational view of an improved monitoring device in accordance with the present invention.

FIG. 8 is a sectional view of a portion of the monitoring device of FIG. 7, taken substantially upon a plane passing through section line 8—8.

FIG. 9 is a bottom plan view of a portion of the monitoring device of FIG. 7, shown with the cover removed.

DESCRIPTION OF THE PREFERRED EMBODIMENT

Figure 3:
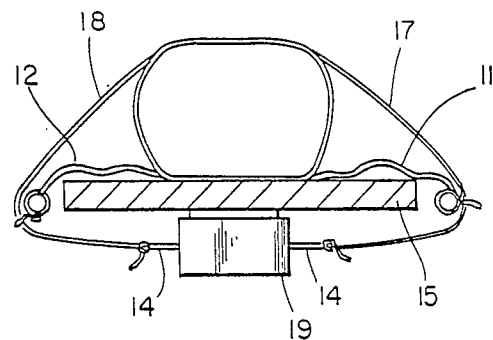
FIG. 3 is a sectional view taken substantially upon a plane passing through section line 3—3.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIGS. 1 and 2, there is shown the vest 10 of the present invention. Vest 10 has an open back and is configured to be disposed about the upper body of a patient who is to be restrained in bed. Important components of vest 10 are tie-straps 11 and 12, which serve somewhat like draw-strings to close vest 10 in the back and draw it up snugly against the patient's body. Tie-straps 11 and 12 also serve to restrain the patient to a bed 15, the tie-straps being anchored to the side-rails 13 of bed 15 by a knot 16 or other suitable fastening means, such as a buckle. The amount of slack remaining in tie-straps 11 and 12 after being anchored to rails 13 determines the limits of the patient's range of movement.

Attached to vest 10 are monitor straps 17 and 18, which are preferably connected to a monitoring device 19 (FIG. 3) located beneath bed 15 that detects and indicates by an alarm excessive movement of the patient. Monitor 19 includes a movable member 14, to which monitor straps 17 and 18 are attached. Movement of movable member 14 beyond a predetermined limit activates the alarm (alarm not shown). Such a monitor is described in U.S. Pat. No. 4,417,572, issued to Green on Nov. 29, 1983. In use, monitor straps 17 and 18 are provided with less slack than tie-straps 11 and 12, thus insuring that the excessive movement monitor 19 will be activated before the patient reaches the limit of his permissible range of movement. A nurse or other monitoring personnel will therefore be alerted before the patient is in any danger of falling out of bed or otherwise harming himself by excessive movement.

Figure 4:
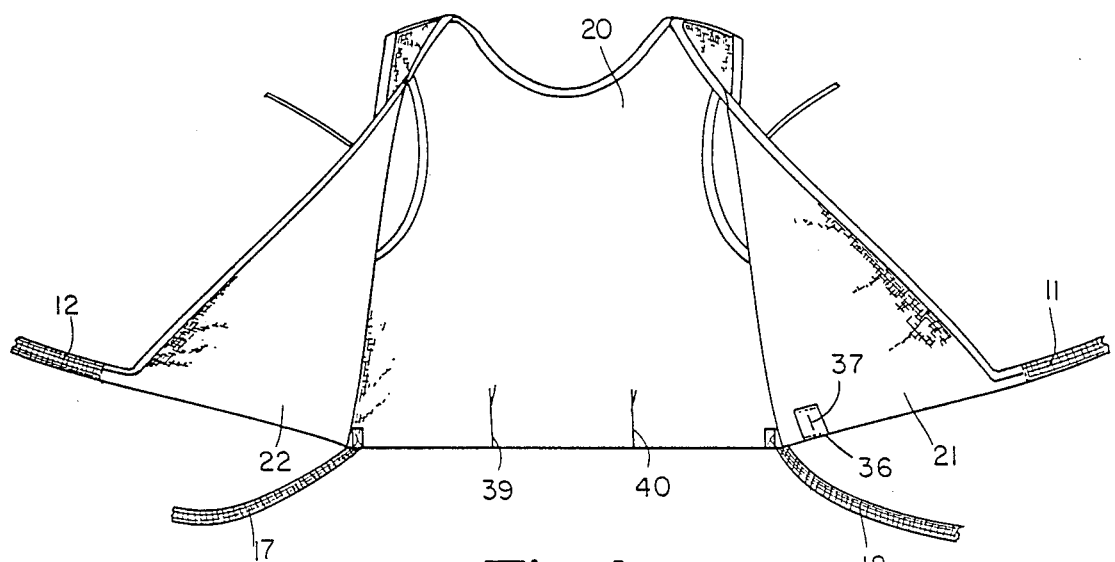
FIG. 4 is an elevational view of the interior of the restraining vest, particularly showing the darts in the front panel and the reinforced slot in one of the posterior wings.

Vest 10 includes a front panel 20 which covers the patient's chest. Front panel 20 is provided with darts 39 and 40 (FIG. 4) stitched therein to provide a slight taper at the waist of the vest. Integral with front panel 20 are posterior wings 21 and 22 which overlap in back to close the vest. Posterior wings 21 and 22 have integral shoulder straps 23 and 24 which are sewed at 25 and 26 to front panel 20, thus forming arm holes 27 and 28 and neck opening 29. Vest 10 may be of any cloth-like fabric, although cotton or a cotton-polyester blend is preferred.

The bottom edge 30 of vest 10 is provided with a belt 32 of woven cloth-like material having a high tensile strength. Belt 32 is sewed to vest 10 continuously along its length. The ends of belt 32 extend beyond ends 33 and 34 of posterior wings 21 and 22 to form integral tie-straps 11 and 12. Multiple stitching, as shown at 31, is employed to reinforce the point of connection between tie-straps 11 and 12 and ends 33 and 34.

Posterior wing 22 is provided with a strip 35 of the same material as belt 32, which is sewn at its top and bottom ends to the underlying fabric of posterior wing 22 to form a loop through which tie-strap 11 is disposed. A similar strip 36 is provided on posterior wing 21, although strip 36 serves only to conceal the underlying slot 37 (FIG. 4) which is provided in posterior wing 21. Tie-strap 12 is disposed through slot 37 from the interior of the vest to the exterior. A strip 44 is provided on the interior surface of panel 20 to reinforce slot 37.

The posterior wings 21 and 22 are provided with tie-cords 41 and 42 at the mid-scapular line, which may be tied together in a bow knot 43 to give additional support to vest 10 to help prevent it from being removed by slipping it over the shoulders.

Referring in particular to FIG. 5, there is shown the detail of the construction of armhole seams 45 and 46, and neck opening seam 47. One edge of a cloth finishing strip 48 is stitched to the edge of the vest fabric at 49. The seam is then reverse folded at 50 with the other edge of strip 48 being reverse folded at 51 and stitched at 52 to provide a neat, ravel free finished seam.

Referring in particular to FIG. 6, there is shown the detail of the construction of the seam at bottom edge 30 of vest 10. The vest fabric is reverse folded at edge 30 and belt 32 is stitched to panel 20 along its edges at 53 and 54.

Referring in particular to FIG. 7, there is illustrated a monitoring device 60 in accordance with the present invention. Monitoring device 60 includes two flat steel bar portions 61 and 62 which can be slid lengthwise with respect to each other to adjust the overall length of monitoring device 60. Wingnuts 63 and 64 pass through longitudinal slots in bars 61 and 62 and permit the two bars to be secured together at any selected length within the range of adjustability provided by the length of the slots and the dimensions of bars 61 and 62. The terminal end 65 of bar 61 is bent around into a U-shape suitably sized to hook around the side rail of a typical hospital bed when monitor device 60 is located beneath the bed. Likewise, terminal end 66 of bar 62 is also bent around into a U-shape to hook around the opposite side rail of the hospital bed. When installing monitoring device 60, wing nuts 63 and 64 are loosened, bars 61 and 62 are spread outward, the terminal ends 65 and 66 are hooked around the side rails of the bed, and then bars 61 and 62 are pushed inwardly to tightly engage the side rails of the bed, whereupon wingnuts 63 and 64 are tightened to secure monitoring device 60 to the bed.

Situated intermediate terminal ends 65 and 66 are two pivoted U-shaped levers 69 and 70. Lever 69 pivots on pin 71 which is held between an upwardly humped portion 72 of bar 61 and a flat bar portion 73 spotwelded therebelow to bar 61. Lever 70 is similarly pivoted on pin 76 which is held between an upwardly humped portion 77 of bar 61 and bar 62 located therebelow. Inasmuch as it is the humped portions 72 and 77 which restrain the pivot pins 71 and 76 from moving longitudinally with respect to the monitoring device 60, and since they are both part of bar 61, the distance between the pivots of levers 69 and 70 remain constant despite adjustment of the overall length of monitoring device 60 by moving bars 61 and 62 with respect to each other.

Attached to bar 61 between levers 69 and 70 is switch box 78, which includes two movable elements 79 and 80 which are mounted to move longitudinally. Element 79 is connected to pin 81 of lever 69 by cable 82, and element 80 is connected to pin 85 of lever 70 by cable. In use, monitor straps 17 and 18 are passed through loops 87 and 88 and attached to levers 69 and 70, respectively, by slip knots. Tension in straps 17 or 18 causes levers 69 or 70 to pivot outwardly, thereby pulling on cables 82 or 86, which in turn causes moveable elements 79 and 80 to move outwardly, which actuates the alarm activation means associated with switch box 78, as described below.

Referring in particular to FIG. 8, it may be seen that lever 69 is provided with a third pin 91 located below flat bar portion 73. Surrounding pin 91 is a rubber bushing 92 which engages bar portion 73. When lever 69 is pivoted about pin 71, pin 91 is necessarily caused to move upwardly, which causes bushing 92 to be compressed between pin 91 and bar portion 73. This provides a resilient resistance to the pivotal displacement of lever 69. Consequently, any tension applied to strap 17 must be of sufficient magnitude to compress bushing 92 enough to allow lever 69 to pivot far enough to activate switch box 78. In other words, not every pull on strap 17 will activate switch box 17, but only such pulls as exceed a predetermined level of tension, which can be selected by substituting bushings of various densities. This action prevents false alarms from slight movement of the patient which does not amount to an attempt to escape. Lever 70 is provided with a similar bushing which acts in a similar way.

Referring to FIG. 9, it may be seen that elements 79 and 80 are in fact toothed racks engaging a common pinion gear 93 which rotates about a pivot pin 94 fixed to switch box 78. A tension spring 95 biases element 80 inwardly, and through the action of pinion gear 93, likewise biases element 79 inwardly. Consequently, pulling force applied to either one of elements 79 or 80 by cables 82 or 86 causes element 80 to move outwardly. Upon such movement, tab 98 of element 80 engages wheel 99 of electrical microswitch 100, thereby activating it. Microswitch 100 is a DPST normally open switch. One pole of microswitch 100 is connected in series with a 9 volt battery 101, a piezoelectric buzzer 102, and a SPST slide switch 103 which acts as a manual on-off switch. When switch 103 is on, then activation of microswitch 100 causes buzzer 102 to emit an audible alarm signal. The other pole of microswitch 100 is connected in series with the contacts of a ¼ inch phone jack 104, which is in turn wired in parallel with a ⅛ inch mini phone jack 105. Activation of microswitch 100 provides a closed circuit across the terminals of jacks 104 and 105, which jacks can be connected via an appropriate adapter to the nurse call system of a hospital or nursing home, or alternatively to a stand-alone alarm system having its own proper supply and audible signal, such as might be used for remote signalling in in-home use or for use in nursing facilities not having a central nurse call system.

While the preferred embodiment of the invention has been illustrated and described in some detail in the drawings and foregoing description, it is to be understood that this description is made only by way of example to set forth the best mode contemplated of carrying out the invention and not as a limitation to the scope of the invention which is pointed out in the claims below.

What is claimed is:

1. A patient monitoring device for attachment beneath a bed frame having side rails, for use with a patient restraint garment, comprising:

an elongate attachment bar having a U-shaped first end for hooking to one side rail of said bed frame and having a U-shaped second end for hooking to the other side rail of said bed frame;

a first lever having first and second ends, the first end attached to said attachment bar for pivotal motion about a pivot axis perpendicular to said elongate attachment bar, the second end configured for attachment to a portion of said patient restraint garment;

a second lever having first and second ends, the first end attached to said attachment bar for pivotal motion about a pivot axis perpendicular to said elongate attachment bar, the second end configured for attachment to a portion of said patient restraint garment; and a switch box attached to said attachment bar intermediate said first and second levers, said switch box having first and second movable elements mounted to move longitudinally with respect to said elongate attachment bar, the first movable element being connected to said first lever intermediate the first and second ends of said first lever, the second movable element being connected to said second lever intermediate the first and second ends of said second lever, said switch box including an electrical switch activated by movement of any of the first and second moveable elements beyond a selected displacement.

2. The patient monitoring device of claim 1, in which each of said first and second levers include resilient stop means for providing increasing resistance to pivotal movement as said lever is pivoted toward said elongate attachment bar.

3. The patient monitoring device of claim 1, in which said elongate attachment bar is comprised of two sections longitudinally slidable with respect to each other for adjusting the length thereof, and includes means for holding the two sections together at a selected length.

4. The patient monitoring device of claim 3, in which the locations of the first lever pivot, the second lever pivot, and the switch box are fixed with respect to each other and with respect to one of the two sections of said elongate attachment bar, whereby adjustment of the length of said attachment bar by sliding the two sections thereof with respect to each other does not affect the spatial relationships between the first lever, second lever, and switch box.

5. The patient monitoring device of claim 1, in which the first and second movable elements of said switch box each include a toothed rack engaging a common pinion gear therebetween, such that longitudinal movement of one movable element causes an equal and oppositely directed longitudinal movement of the other movable element.

6. The patient monitoring device of claim 5, in which one of said movable elements of said switch box includes a protruding tab which activates the electrical switch.

7. The patient monitoring device of claim 5, in which said switch box includes a spring connected to said switch box and to at least one of the two movable elements to bias the movable elements in a inward disposition.

8. A patient restraint device for restraining a patient on a bed against excessive vertical and horizontal movement with respect to said bed, said bed having a frame with side rails, and for activating an electrical alarm upon occurrence of said excessive movement, comprising:

a garment configured to be secured to the patient, said garment having a pair of straps extending therefrom, one of said pair of straps extendable over one side of the bed, and the other of said pair of straps extendable over the other side of the bed;

an elongate attachment bar having a U-shaped first end for hooking to one side rail of said bed frame and having a U-shaped second end for hooking to the other side rail of said bed frame such that said attachment bar is attachable to said bed therebeneath;

a first lever having first and second ends, the first end attached to said attachment bar for pivotal motion about a pivot axis perpendicular to said elongate attachment bar, the second end configured for attachment to one of said pair of garment straps;

a second lever having first and second ends, the first end attached to said attachment bar for pivotal motion about a pivot axis perpendicular to said elongate attachment bar, the second end configured for attachment to the other of said pair of garment straps; and a switch box attached to said attachment bar intermediate said first and second levers, said switch box having first and second movable elements mounted to move longitudinally with respect to said elongate attachment bar, the first movable element being connected to said first lever intermediate the first and second ends of said first lever, the second movable element being connected to said second lever intermediate the first and second ends of said second lever, said switch box including an electrical switch activated by movement of any of the first and second moveable elements beyond a selected displacement, the electrical switch being connectable to an external electrical alarm circuit;

whereby excessive movement of said patient with respect to said bed creates tension in at least one of said garment straps, thereby pivoting at least one of said levers and activating the electrical switch of said switch box.

* * * * *